United States Patent [19]

George et al.

[11] Patent Number: 4,847,263

[45] Date of Patent: Jul. 11, 1989

[54] IMIDAZOPYRIDINE DERIVATIVES AND COMPOSITIONS CONTAINING THEM

[75] Inventors: Pascal George, Vitry sur Seine; John Allen, Voisins le Bretonneux; Guy Jaurand, Morsang sur Orge; Daniéle De Peretti, Antony, all of France

[73] Assignee: Synthelabo, France

[21] Appl. No.: 173,813

[22] Filed: Mar. 28, 1988

[30] Foreign Application Priority Data

Mar. 27, 1987 [FR] France ................. 87 04276
Mar. 27, 1987 [FR] France ................. 87 04277

[51] Int. Cl.$^4$ ............. A61K 31/44; C07D 471/04
[52] U.S. Cl. ........................... 514/300; 546/121
[58] Field of Search ................... 546/121; 514/300

[56] References Cited

U.S. PATENT DOCUMENTS

| | | | |
|---|---|---|---|
| 3,978,071 | 8/1976 | Nakanishi et al. | 546/121 |
| 4,221,796 | 9/1980 | Wade et al. | 546/121 |
| 4,382,938 | 5/1983 | Kaplan et al. | 546/121 |
| 4,650,796 | 3/1987 | George et al. | 514/213 |

FOREIGN PATENT DOCUMENTS

0172096  7/1985  European Pat. Off. ............ 546/121

OTHER PUBLICATIONS

Kaminski et al., Chemical Abstracts, vol. 103, No. 1, Abstract No. 192j; Jul. 8, 1985, p. 18.

*Primary Examiner*—Mary C. Lee
*Assistant Examiner*—Zinna Northington
*Attorney, Agent, or Firm*—Wegner & Bretschneider

[57] ABSTRACT

Imidazo[1,2-a]pyridine derivatives of the general formula (I)

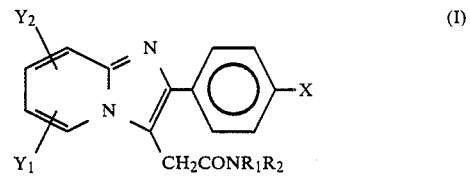

wherein $Y_1$ represents hydrogen, halogen or $(C_{1-4})$ alkyl, $Y_2$ represents —SR in which R is hydrogen, $(C_{1-4})$ alkyl or (4-alkoxyphenyl)methyl or hydroxy or $(C_{1-4})$ alkoxy, X represents hydrogen, halogen, $(C_{1-4})$ alkoxy, $(C_{1-4})$ alkyl, —CF$_3$, —CH$_3$S, —NO$_2$ or —NH$_2$, and $R_1$ and $R_2$, which may be the same or different, represent hydrogen or $(C_{1-4})$ alkyl have useful therapeutic properties.

6 Claims, No Drawings

IMIDAZOPYRIDINE DERIVATIVES AND COMPOSITIONS CONTAINING THEM

The present invention relates to imidazopyridine derivatives and to pharmaceutical compositions containing them.

According to the invention there are provided imidazo[1,2-a]pyridine derivatives of the general formula (I)

wherein $Y_1$ represents hydrogen, halogen or $(C_{1-4})$ alkyl, $Y_2$ represents -SR in which R is hydrogen, $(C_{1-4})$ alkyl or (4-alkoxyphenyl)methyl or hydroxy or $(C_{1-4})$ alkoxy, X represents hydrogen, halogen, $(C_{1-4})$ alkoxy, $(C_{1-4})$ alkyl, $-CF_3$, $CH_3S$, $-NO_2$ or $-NH_2$, and $R_1$ and $R_2$, which may be the same or different, represent hydrogen or $(C_{1-4})$ alkyl.

Preferred compounds of the invention are those in which $Y_1$ is at the 6-position and represents halogen, $Y_2$ is at the 8-position and represents -SR in which R is H, $(C_{1-4})$ alkyl or (4-alkoxyphenyl)methyl, or hydroxy or $(C_{1-4})$ alkoxy, X represents halogen or $(C_{1-4})$ alkyl, and $R_1$ and $R_2$ are as defined above, and more especially those wherein $Y_1$ is chlorine, $Y_2$ is methylthio, mercapto, methoxy, hydroxy, n-butylthio or (4-methoxyphenyl)methylthio, X is chlorine or methyl, and $R_1$ and $R_2$ are each methyl or n-propyl.

Other compounds of interest are those wherein $Y_1$ is hydrogen, $Y_2$ is at the 6-position and represents —S—alkyl or alkoxy, X represents halogen or $(C_{1-4})$ alkyl, and $R_1$ and $R_2$ are as defined above, and more especially those wherein $Y_2$ is methylthio or alkoxy, X is chlorine or methyl, and $R_1$ and $R_2$ are each methyl or n-propyl.

The compounds of the invention can be prepared by processes that differ according to the substituents $Y_1$ and/or $Y_2$.

The compounds of the invention in which $Y_2$ is 8-SR are prepared according to the reaction scheme given in Appendix 1: a 2-aminopyridine of formula (II) is brominated, and the bromo compound (III) is then reacted with a bromo ketone of formula (IV), the imidazopyridine of formula (V) obtained is reacted with an acetal of formula (VI), the compound of formula (VII) obtained is treated using $SOCl_2$, and the chloro compound obtained is then reduced in situ with an agent such as Rongalite; the compound (VIII) is reacted with a sodium alkylthiolate, prepared in dimethylformamide from an alkylthiol and sodium hydride, and an S-alkyl derivative (I) is then obtained.

The compound (I) in which $Y_2$ is 8-SH is prepared from the compound (VIII): this compound (VIII) is reacted with 4-methoxybenzenemethanethiol in dimethylformamide in the presence of sodium hydride, to obtain a compound bearing a 4-methoxybenzylthio radical in place of the bromine atom. This compound is stirred at 0° C. in trifluoroacetic acid and in the presence of mercury acetate to obtain the thiol (I) in the form of the mercury thiolate.

The disulfide of the compound can be obtained by treating the mercury thiolate with trifluoroacetic acid and hydrogen sulfide.

The compounds of the invention in which $Y_2$ is 8-alkoxy and 8-OH are prepared according to the reaction scheme in Appendix 2: a compound (V), the preparation of which is described in Appendix 1, is reacted with a sodium alkoxide in hexamethylphosphorotriamide, and the methoxylated compound (X) is then reacted with 1,1-diethoxy-N,N-$(R_1R_2)$acetamide, after which the compound (XI) obtained is converted in the presence of $SOCl_2$ and then Rongalite to the alkoxylated compound (I); the corresponding compound (I) in which $Y_2$ is OH is obtained by the action of $BBr_3$ on the alkoxylated compound (I).

The compounds of the invention in which $Y_2$ is 6-alkoxy or 6-SR are prepared according to the reaction scheme given in Appendix 3: the 2-aminopyridine of formula (XII) is condensed with an α-bromoacetophenone of formula (XIII), and the imidazopyridine of formula (XIV) obtained is then condensed with the glyoxamide acetal of formula (VI); the α-hydroxyamide (XV) is treated with $SOCl_2$ and the compound obtained is then reduced using Rongalite to obtain the compound of formula (I).

The 5-alkoxypyridinamines (XII) are obtained according to the method described by G. J. Clark and L. W. Deady, Aust. J. Chem. 34, 927 (1981).

The 5-alkylthiopyridinamines (XII) are obtained according to the method described by Zelinskii Org. Chem. Inst. Derwent 79-88949 B (49).

The examples which follow illustrate the invention.

The analyses and the IR and NMR spectra confirm the structure of the compounds.

EXAMPLE 1

6-Chloro-2-(4-chlorophenyl)-8-methylthio-N,N-dipropylimidazo[1,2-a]pyridine-3-acetamide 1.1. 2-Amino-3-bromo-5-chloropyridine 20 g (77.8 mmol) of 2-amino-5-chloropyridine dissolved in 160 ml of $CH_2Cl_2$ are reacted with 8 ml of bromine, which is added dropwise at 0° C. After the addition is complete, the mixture is left to react at 25° C. for 2 h. The suspension is washed with 10% strength sodium hydroxide solution, and the organic phase is washed with water and then dried over $MgSO_4$, filtered and evaporated. The compound obtained is recrystallized in isopropanol. M.p. 82° C.

1.2. 8-Bromo-6-chloro-2-(4-chlorophenyl)imidazo[1,2-a]-pyridine 17 g (82 mmol) of 2-amino-3-bromo-5-chloropyridine dissolved in 150 ml of ethanol are reacted with 29 g of 2-bromo-1-(4-chlorophenyl)-1-ethanone and 14 g of sodium hydrogen carbonate. The mixture is brought to the refluxing temperature for 6 h and cooled. The precipitate is filtered off and rinsed with $CH_2Cl_2$, and the filtrate is concentrated under reduced pressure. After recrystallization of the evaporation residue in ethyl acetate, the compound melts at 178° C.

1.3. 8-Bromo-6-chloro-2-(4-chlorophenyl)-α-hydroxy-N,N-dipropylimidazo[1,2-a]pyridine-3-acetamide A solution of 2.03 g of 1,1-diethoxy-N,N-dipropylacetamide is prepared in 30 ml of glacial acetic acid and 0.1 ml of 37% strength hydrochloric acid. The solution is brought to 60° C. for 2 h. 312 mg of sodium acetate are added to the solution followed, after 10 min., by 2.9 mmol of the compound obtained above under 1.2. The reaction mixture is brought to 60° C. for approximately 3 h, the acetic acid is evaporated off, water is added and the mixture is then extracted with $CH_2Cl_2$. The organic phase is dried over $MgSO_4$ and filtered and the filtrate concentrated under reduced pressure. After recrystallization of the evaporation residue in ethanol, the compound melts at 199°–200° C.

1.4. 8-Bromo-6-chloro-2-(4-chlorophenyl)-N,N-dipropylimidazo[1,2-a]pyridine-3-acetamide 5 g (10 mmol) of the compound obtained under 1.3, dissolved in 100 ml of $CH_2Cl_2$, are reacted with 2.2 ml of $SOCl_2$. The reaction mixture is heated to 60° C. for 2 h. It is evaporated to dryness under reduced pressure, the residue is taken up with $CHCl_3$, this mixture is again evaporated to dryness and the residue is then dried under vacuum.

The compound obtained is dissolved in $CH_2Cl_2$ and 4.7 g of Rongalite are added; the mixture is maintained at 20° C. for 48 h. Water is added to dissolve the solid formed, and the organic phase is separated after settling has occurred and washed with water, then with 30% strength sodium hydroxide and then with water. The organic phase is dried over $MgSO_4$ and filtered, and the filtrate concentrated under reduced pressure. The evaporation residue is recrystallized in ethanol. M.p. 189°–192° C.

1.5. 6-Chloro-2-(4-chlorophenyl)-8-methylthio-N,N-dipropylimidazo[1,2-a]pyridine-3-acetamide A 5.8 molar solution of methanethiol is prepared in tetrahydrofuran. 1.8 ml of this solution, 2 ml of dimethylformamide (DMF) and 480 mg of 50% strength sodium hydride are mixed at 20° C.

A solution of 2.5 g (5.18 mmol) of the compound obtained under 1.4 in 25 ml of DMF is added slowly. The mixture is stirred at 20° C. for 1 h 30 min. and then at 60° C. for 1 h. Water is added, the organic phase is separated after settling has occurred, dried over $MgSO_4$ and filtered, and the filtrate is evaporated under reduced pressure. The evaporation residue is purified by chromatography on a silica column and the product is recrystallized in isopropanol. M.p. 152°–154° C.

EXAMPLE 2

6-Chloro-2-(4-chlorophenyl)-8-{[(4-methoxyphenyl)-methyl]thio}- and
-8-mercapto-N,N-dipropylimidazo[1,2-a]pyridine-3-acetamides 2.1. Sodium hydride and dimethylformamide are introduced with stirring under argon into a round-bottomed flask, followed, dropwise, by 2 equivalents of 4-methoxybenzenemethanethiol. The mixture is left to react for 50 min. 345 mg (0.17 mmol) of the compound obtained under 1.4. are introduced. After 1 h, the reaction mixture is brought to 40° C. for 1 hour.

It is left to cool, ice and water are added, the mixture is extracted 3 times with ether, the organic phase is washed with water, dried over $Na_2SO_4$ and filtered, and the filtrate is concentrated under reduced pressure. The product obtained is recrystallized in a dichloromethane/ether mixture. M.p. 125°–126° C.

2.2. 111 mg (0.2 mmol) of the compound obtained under 2.1. are introduced into 1 ml of trifluoroacetic acid in the presence of anisole (20 μl). The mixture is treated with 63.8 mg (0.2 mmol) of mercury acetate with stirring, at 0° C., for 15 min. The compound formed is isolated and purified by chromatography on silica with a 95:5 chloroform/methanol eluent. The compound obtained in the form of the mercury thiolate melts at 191°–192° C.

It is also possible to isolate the compound from the mercury thiolate, by the action of trifluoroacetic acid and hydrogen sulphide, in the form of the disulphide which melts at 126°–128° C.

EXAMPLE 3

6-Chloro-2-(4-chlorophenyl)-8-methoxy-N,N-dipropylimidazo[1,2-a]pyridine-3-acetamide 3.1. 6-Chloro-2-(4-chlorophenyl)-8-methoxyimidazo[1,2-a]-pyridine 10 g (29.4 mmol) of 8-bromo-6-chloro-2-(4-chlorophenyl)imidazo[1,2-a]pyridine, the preparation of which compound is described in the patent application filed this day entitled: Dérivés d'imidazopyridines, leur préparation et leur application en thérapeutique (Imidazopyridine derivatives, their preparation and their application in therapy) by the Applicant, dissolved in 60 ml of hexamethylphosphorotriamide, are added to a solution of sodium methylate prepared using 2.03 g of sodium and 15 ml of methanol, the reaction mixture is brought to 60° C. for 2 h 30 min., water is added, the mixture is extracted with $CH_2Cl_2$, the organic phase is washed with water, dried over $MgSO_4$ and filtered, and the filtrate is concentrated under reduced pressure. The evaporation residue is recrystallized in an ethyl acetate/hexane mixture. M.p. 150°–151° C.

3.2. 6-Chloro-2-(4-chlorophenyl)-α-hydroxy-8-methoxy-N,N-dipropylimidazo[1,2-a]pyridine-3-acetamide A solution of 9.46 g of 1,1-diethoxy-N,N-dipropylacetamide is prepared in 135 ml of glacial acetic acid and 0.46 ml of 37% strength hydrochloric acid.

The reaction mixture is heated to 60° C. for 2 h. 1.3 g of sodium acetate are added, followed, after 10 min., by 4 g (13.6 mmol) of the compound obtained under 3.1.

The reaction mixture is heated to 60° C. for 3 h, then cooled and evaporated to dryness.

The residue is taken up with $CH_2Cl_2$, the organic phase is washed with water, dried over $MgSO_4$ and filtered, and the filtrate is concentrated under reduced pressure. The product obtained is purified by chromatography with a 3:1 hexane/ethyl acetate eluent. The compound obtained is used without further treatment for the following stage.

3.3. 6-Chloro-2-(4-chlorophenyl)-8-methoxy-N,N-dipropylimidazo[1,2-a]pyridine-3-acetamide 2.75 g (6.12 mmol) of the compound obtained above, 50 ml of $CH_2Cl_2$ and 1.34 ml of $SOCl_2$ are mixed. The reaction mixture is brought to 60° C. for 2 h and evaporated to dryness, and the residue is then dried under vacuum. 30 ml of pure $CH_2Cl_2$ are added, followed by 2.82 g of Rongalite. The reaction mixture is left at 20° C. overnight.

Water is added to the mixture, the organic phase is separated after settling has occurred, washed with water and then with sodium chloride solution, dried over $MgSO_4$ and filtered, and the filtrate is concentrated under reduced pressure.

The residue is purified by chromatography (eluent: hexane/ethyl acetate 2:1). M.p. 162°–163° C.

EXAMPLE 4

6-Chloro-2-(4-chlorophenyl)-8-hydroxy-N,N-dipropylimidazo[1,2-a]pyridine-3-acetamide 0.2 ml (0.53 g; 2.11 mmol) of BBr$_3$ is added at $-60°$ C. to 0.15 mg (0.36 mmol) of the product obtained under 3.3., dissolved in 15 ml of dichloromethane. The mixture is allowed to return to room temperature, with stirring, during two hours.

The excess BBr$_3$ is then destroyed with methanol at $-78°$ C. The reaction mixture is evaporated and the residue obtained purified by chromatography (eluent: dichloromethane/methanol 95:5). A product is obtained which is crystallized in the form of the base in ethyl acetate. M.p. 190°–191° C.

EXAMPLE 5

8-n-Butylthio-6-chloro-2-(4-chlorophenyl)-N,N-dipropylimidazo[1,2-a]pyridine-3-acetamide 300 mg (2eq) of 50% strength sodium hydride in oil and 30 ml of dimethyl formamide are introduced into a three-necked round-bottomed flask, with mechanical stirring, under argon, and cooled using an ice bath, followed, dropwise, by 600 μl (2eq) of butanethiol, and the mixture is stirred for 45 min. Using a dropping funnel, 1.5 g (3.10 mmol) of 8-bromo-6-chloro-2-(4-chlorophenyl)-N,N-dipropylimidazo[1,2-a]pyridine-3-acetamide in 30 ml of dimethylformamide are added. The mixture is allowed to return to room temperature and is stirred for 3 hours.

After the mixture is cooled, ice is added slowly, followed by water.

The mixture is extracted 3 times with ether and the organic phase is washed once with water, dried over magnesium sulphate, filtered and evaporated to dryness.

After chromatography on silica gel, with a 99.5:0.5 CH$_2$Cl$_2$/methanol eluent, the compound melts at 119°–120° C.

EXAMPLE 6

2-(4-Chlorophenyl)-6-methoxy-N,N-dimethyl-imidazo[1,2-a]pyridine-3-acetamide 6.1. 2-(4-Chlorophenyl)-6-methoxyimidazo[1,2-a]pyridine A mixture of 1.3 g (10.5 mmol) of 5-methoxy-2-pyridinamine, 2.44 g (1eq) of α-bromo-4-chloroacetophenone and 1.76 g (2eq) of sodium bicarbonate in 20 ml of 95% strength alcohol is heated under reflux for 4 h 30 min. under argon. The mixture is evaporated to dryness and the residue taken up between CH$_2$Cl$_2$ and H$_2$O, followed by washing, drying and evaporation. The product is purified by chromatography and then crystallized in ether. M.p. 148°–9° C.

5-Methoxy-2-pyridinamine was obtained according to a process described in the literature: G. J. Clark and L. W. Deady, Aust. J. Chem. 34, 927 (1981).

6.2. 2-(4-Chlorophenyl)-α-hydroxy-6-methoxy-N,N-dimethylimidazo[1,2-a]pyridine-3-acetamide A solution of 4.95 g (26.7 mmol) of 1,1-diethoxy-N,N-dimethylacetamide is prepared in 90 ml of acetic acid. The mixture is heated to 50° C., 0.7 ml of 37% strength hydrochloric acid is added and the mixture is stirred for 2 h at this temperature. 2.2 g (27.7 mmol) of sodium acetate are added, followed, after 15 min., by 2.3 g (8.9 mmol) of the compound obtained in 6.1. Heating is continued for 2 h. The mixture is evaporated to dryness, the residue is taken up between CH$_2$Cl$_2$ and ammonia water, the organic phase is washed, dried and evaporated and the product is crystallized in ethyl ether. 2.2 g of white solid are obtained. M.p. 185°–186° C. (dec.). The compound contains 0.7% of water.

6.3. 2-(4-Chlorophenyl)-6-methoxy-N,N-dimethylimidazo[1,2a]pyridine-3-acetamide 2.1 g (5.8 mmol) of the compound obtained in 6.2. are dissolved in 115 ml of CH$_2$Cl$_2$, 11.5 ml of thionyl chloride are added and the mixture is stirred for 15 h at room temperature. It is then evaporated to dryness, the residual solid is taken up with pentane and the solid obtained is dried under vacuum. 2.4 g of this compound are dissolved in 180 ml of CH$_2$Cl$_2$, 2.67 g (3eq) of Rongalite are added and the mixture is stirred for 20 h at room temperature. The solid obtained is filtered off and purified by chromatography, and it is then crystallized in ether. M.p. 170°–2° C. (dec.).

The compounds for which Y$_2$ is SCH$_3$ at the 6-position are prepared according to the same procedure, from 5-methylthio-pyridinamine according to the scheme in Appendix 3.

The compounds prepared by way of examples are listed in the following table.

TABLE

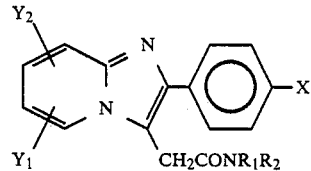

| Compound | Y$_1$ | Y$_2$ | X | R$_1$ = R$_2$ | m.p. (°C.) |
|---|---|---|---|---|---|
| 1 | 6-Cl | 8-SCH$_3$ | Cl | nC$_3$H$_7$ | 152–154 |
| 2 | 6-Cl | 8-SH | Cl | nC$_3$H$_7$ | 191–192* |
| 3 | 6-Cl | 8-OCH$_3$ | Cl | nC$_3$H$_7$ | 162–163 |
| 4 | 6-Cl | 8-OH | Cl | nC$_3$H$_7$ | 190–191 |
| 5 | 6-Cl | 8-S—nC$_4$H$_9$ | Cl | nC$_3$H$_7$ | 119–120 |
| 6 | 6-Cl | 8-SCH$_2$C$_6$—H$_4$OCH$_3$ | Cl | nC$_3$H$_7$ | 125–126 |
| 7 | H | 6-OCH$_3$ | Cl | CH$_3$ | 170–172 |
| 8 | H | 6-SCH$_3$ | CH$_3$ | CH$_3$ | 119–121 |
| 9 | H | 6-SCH$_3$ | Cl | CH$_3$ | 146–147 |

*Hg$^{++}$ thiolate

Compounds of the invention were subjected to pharmacological trails which showed their advantageous pharmacological properties in various fields.

The toxicity of the compounds was determined intraperitoneally in mice.

The DL$_{50}$ ranges from 500 to 1,000 mg/kg.

The sedative or hypnotic activity was determined by observing the action of the compounds on the ECoG of curarized rats [Depoortere H., Rev. E.E.G. Neurophysiol., (1980) 10, 3, 207–214]. In immobilized rats, the test products are injected intraperitoneally or orally at increasing doses from 1 to 30 mg/kg. They induce sleep traces at doses equal to or greater than 0.3 mg/kg i.p.

The anticonvulsant activity of the compounds was determined according to the test of inhibition of pentetrazol-induced clonic convulsions in mice, according to the method of Worms et al. (J. Pharmacol. Exp. Ther., 220: 660–671). In Charles River CD1 male mice (20–22 g), clonic convulsions are induced by the i.v. injection of 35 mg/kg of pentetrazol, 30 min after the i.p. injection of the test product.

The AD$_{50}$ is the dose which protects 50% of the animals against pentetrazol-induced clonic convulsions. The AD$_{50}$ of the compounds of the invention ranges from 0.1 to 10 mg/kg. Effects on the sodium 4-hydroxybutyrate-induced "sleep" time.

This action was determined by the influence of a compound on the sodium 4-hydroxybutyrate (GBH)-induced "sleep" time in curarized rats.

The animals used are Charles River Strain male rats weighing 200±20 g. The animals, immobilized with alloferin administered i.p. in the proportion of 5 mg/kg, are placed under artificial respiration using a mask applied on the muzzle (respiratory rate=50/minute; volume 14 ml).

The oesophagus is ligatured beforehand in order to avoid the entry of air into the stomach.

Frontoparietal and occipital cortical electrodes enable the electrocorticographic activity to be recorded on a Grass model 79 P polygraph at the rate of 6 mm/sec.

The preparation of the animal is performed under local anaesthetic (2% strength xylocaine). The rats are maintained at a constant temperature (37.5° C.) throughout the experiment. Ten minutes after the preparation of the rat is complete, a dose of 200 mg/kg of sodium 4-hydroxybutyrate is injected intravenously into the tail.

A dose of 10 mg/kg of the test compound is administered intraperitoneally 3 minutes after the administration of the sodium 4-hydroxybutyrate.

The assessment of the traces is carried out on the basis of 15-minute periods during 75 minutes after the injection of GHB. During this period of analysis, the total "sleep" time is determined. A series of 15 controls enables the "GHB sleep" time to be specified.

A statistical analysis of the results is carried out using the Mann-Whitney "U" test.

Some compounds reduce the effects of GHB (up to 40% decrease in the sleep time at a dose of 10 mg/kg), while others potentiate these effects (up to 40% increase at a dose of 10 mg/kg). It is also found that the effects can be opposite according to whether the compounds are administered at high doses or at low doses.

The results of the pharmacological trials show that the compounds of the invention are active in the central nervous system field, and possess anxiolytic, sleep-inducing, hypnotic and anticonvulsant properties; the compounds of the invention are useful for the treatment of anxiety states, sleep disorders and other neurological and psychiatric conditions.

The compounds of the invention also show a very high affinity for the peripheral type benzodiazepine binding sites ($\omega_3$). This activity is determined according to the method described in the literature by S. Arbilla, H. Depoortere, P. George, S.2. Langer Nauyn Schmiedeberg's Archiv. Pharmacol. 330, 248-251 (1985).

The $IC_{50}$ values (concentrations which inhibit 50% of the binding of tritiated Ro5-4864 in the kidney membranes) of compounds of the invention range from 0.01 to 100 nanomolar.

The compounds can hence be useful in the following fields:

in the immune system, as immunomodulators such as immunostimulants or immunosuppressants for the regulation of cell proliferation in the cardiovascular system, as coronary vasodilators and/or protectors in cardiac ischaemia in the central nervous system (action on tissue defence mechanisms and the control of the regeneration of areas affected after lesions of various origins)

in the bronchopulmonary system, as bronchodilators in dermatology (regulation of cell proliferation in the proliferative layer of the epidermis, and modulation of the activity of the sebaceous glands).

The compounds of the invention may be presented in any form suitable for oral or parenteral or topical administration, for example in the form of tablets, dragees, ointments, gelatin capsules, solutions to be taken by mouth or injectable solutions, and the like, with any suitable excipient.

The daily dosage can range from 0.5 to 2,000 mg.

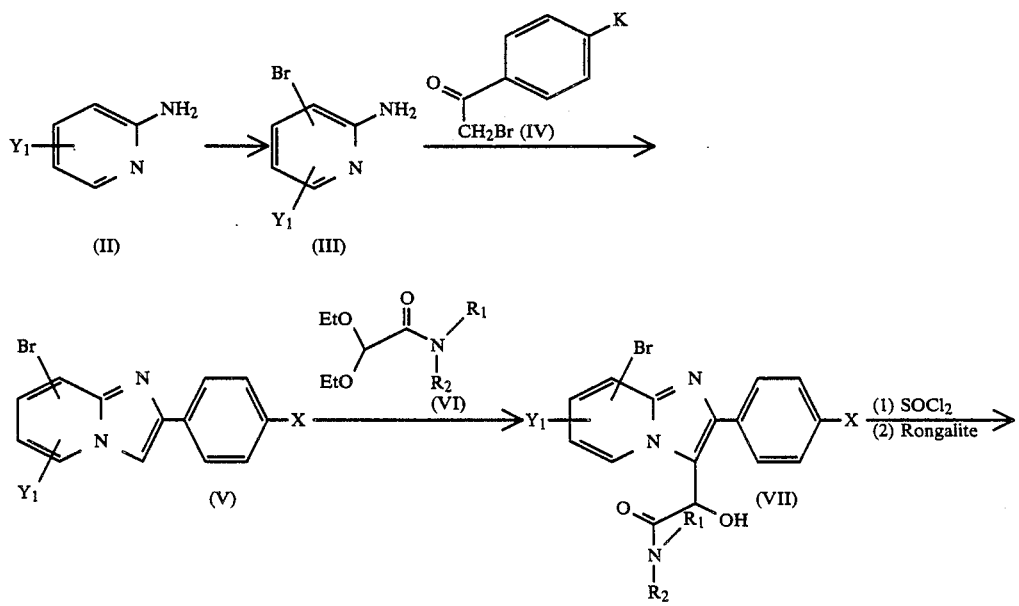

Appendix 1

-continued
Appendix 1
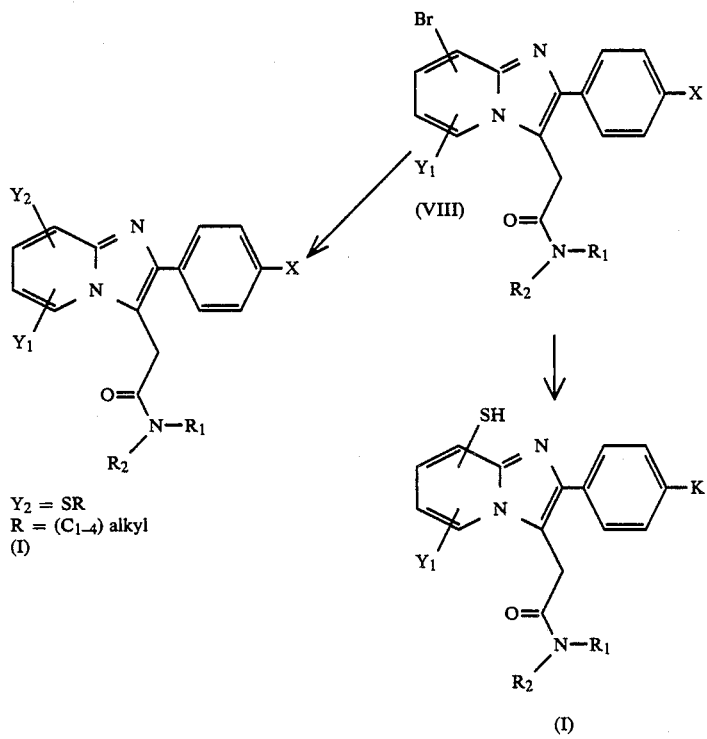
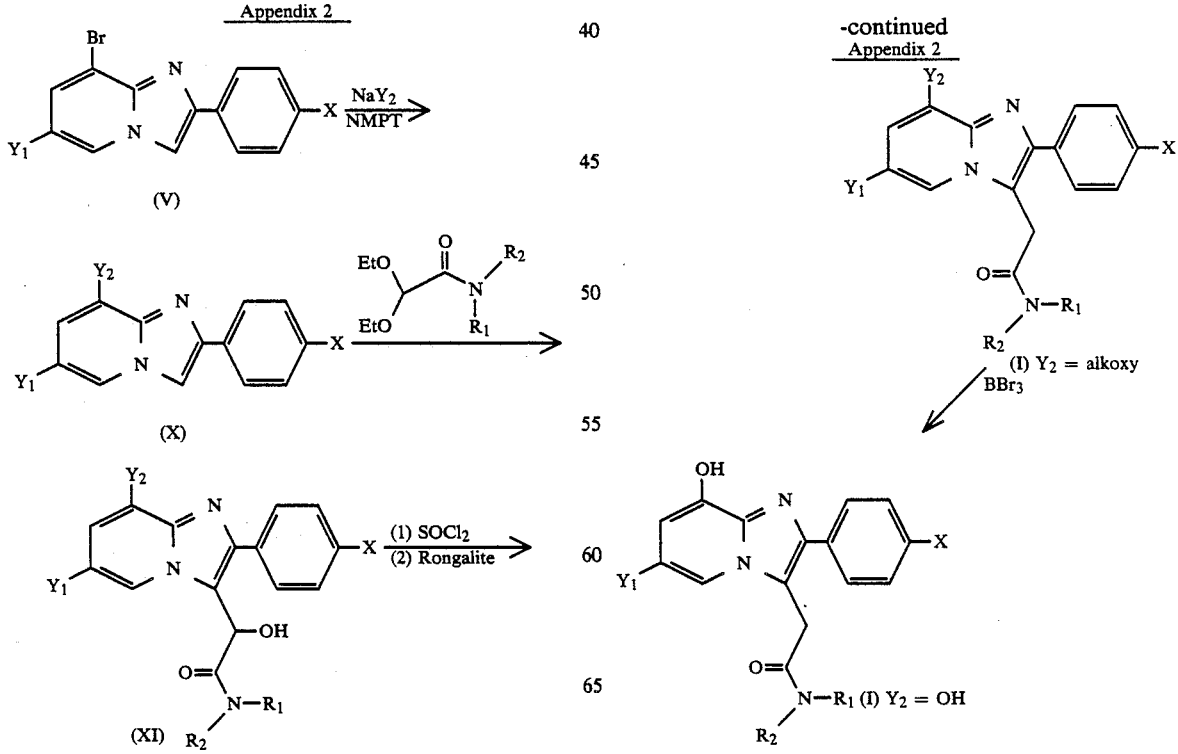

Appendix 3

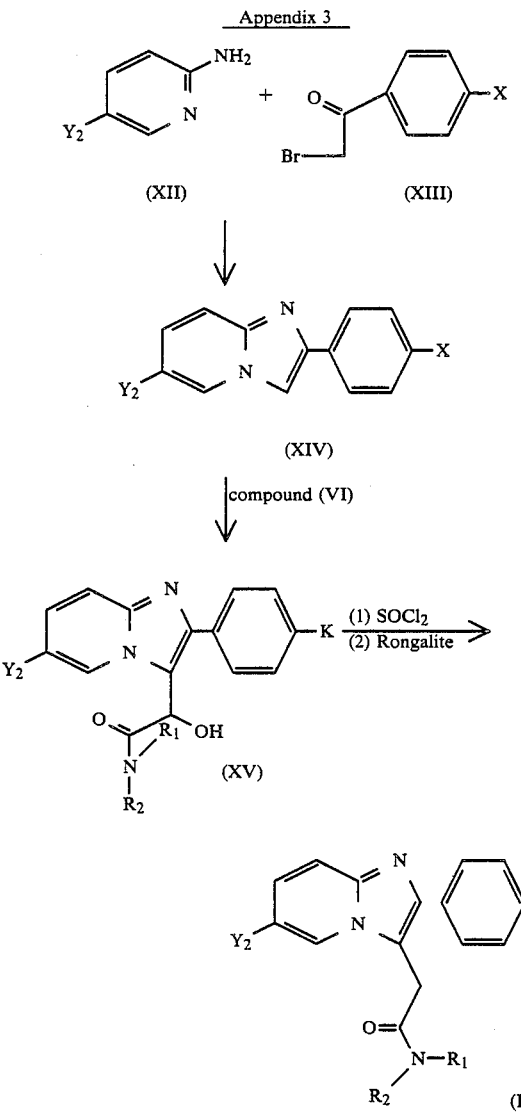

We claim:

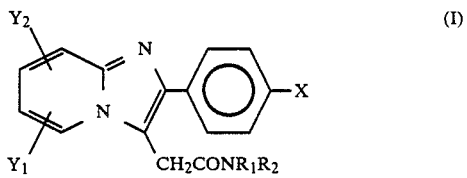

1. A compound of the formula (I)

wherein $Y_1$ is selected from the group consisting of hydrogen, halogen and ($C_{1-4}$) alkyl, $Y_2$ is —SH, —S—($C_{1-4}$) alkyl, —S—$CH_2$—(4-alkoxyphenyl), OH or ($C_{1-4}$) alkoxy, X is selected from the group consisting of hydrogen, halogen, ($C_{1-4}$) alkoxy, ($C_{1-4}$) alkyl, $CF_3$, $CH_3S$, $NO_2$ and $NH_2$, and $R_1$ and $R_2$, which may be the same or different, are selected from hydrogen and linear or branched ($C_{1-4}$) alkyl.

2. Compound according to claim 1, wherein $Y_1$ is at the 6-position and represents halogen, $Y_2$ is at the 8-position and is either a SR group in which R is selected from H, ($C_{1-4}$) alkyl and (4-alkoxyphenyl)methyl, or a hydroxy group or a ($C_{1-4}$) alkoxy group, X is selected from halogen and ($C_{1-4}$) alkyl, and $R_1$ and $R_2$ are as defined in claim 1.

3. Compound according to claim 2, wherein $Y_1$ is chlorine, $Y_2$ is selected from methylthio, mercapto, methoxy, hydroxy, n-butylthio and (4-methoxyphenyl)methylthio, X is selected from chlorine and methyl, and $R_1$ and $R_2$ are each selected from methyl and n-propyl.

4. Compound according to claim 1, wherein $Y_1$ is hydrogen, $Y_2$ is at the 6-position and is selected from —S—($C_{1-4}$) alkyl and ($C_{1-4}$) alkoxy, X is selected from halogen and ($C_{1-4}$) alkyl, and $R_1$ and $R_2$ are as defined in claim 1.

5. Compound according to claim 4, wherein $Y_2$ is selected from methylthio and methoxy, X is selected from chlorine and methyl, and $R_1$ and $R_2$ are each selected from methyl and n-propyl.

6. Pharmaceutical composition for anxiety states and sleep disorders, which contains as active ingredient an effective anxiolytic or sleep-inducing amount of a compound as claimed in claim 1 in association with a pharmaceutically acceptable excipient.

* * * * *